United States Patent [19]

Zabara

[11] Patent Number: 5,025,807

[45] Date of Patent: * Jun. 25, 1991

[54] NEUROCYBERNETIC PROSTHESIS

[76] Inventor: Jacob Zabara, Apartment 19F, 200 Locust St., Philadelphia, Pa. 19106

[*] Notice: The portion of the term of this patent subsequent to Oct. 27, 2004 has been disclaimed.

[21] Appl. No.: 301,111

[22] Filed: Jan. 25, 1989

Related U.S. Application Data

[60] Division of Ser. No. 113,601, Oct. 26, 1987, Pat. No. 4,867,164, which is a continuation-in-part of Ser. No. 814,846, Dec. 30, 1985, Pat. No. 4,702,254, which is a continuation-in-part of Ser. No. 531,955, Sep. 14, 1983, abandoned.

[51] Int. Cl.$^5$ .............................................. A61N 1/32
[52] U.S. Cl. .................................................. 128/421
[58] Field of Search ........... 128/419 C, 419 E, 419 R, 128/421, 42 L, 423 R

[56] References Cited

U.S. PATENT DOCUMENTS

| | | | |
|---|---|---|---|
| 3,296,221 | 3/1967 | Hagfars | 128/421 |
| 3,650,277 | 3/1972 | Sjostrand | 128/419 C |
| 3,850,161 | 11/1974 | Liss | 128/422 |
| 3,918,461 | 11/1975 | Cooper | 128/422 |
| 4,702,554 | 10/1987 | Zabara | 128/421 |
| 4,867,164 | 9/1989 | Zabara | 128/421 |

OTHER PUBLICATIONS

Bilgutay et al, "Vagal Tuning", J. Thoracic & Card Surg., vol. 56, No. 1, Jul. 1968, pp. 71-82.
Neustadt et al, "Implanted Corodoid . . . Hypertension", Surgical Forum, pp. 123-127, 1966.
Peters et al., "The Principle of Elect. Carotoid . . . Therapy", A. Bromed Eng, vol. 8, No. 4-6; pp. 445-458, 1980.

Primary Examiner—Lee S. Cohen
Attorney, Agent, or Firm—Norman E. Lehrer

[57] ABSTRACT

A neurocybernetic prosthesis for controlling or preventing epileptic seizures and other motor disorders includes a pulse generator which generates electrical pulses having a frequency of between 30 and 300 cycles per second, a pulse duration of between 0.3 and 1 millisecond and a constant current of between 1 and 20 milliamperes. The generator is enclosed in an epoxy-titanium shell and is implanted in the body, preferably in the axilla. Electrode leads pass from the generator through a subcutaneous tunnel and terminate in an electrode patch on the vagus nerve. Provisions are made for varying the electrical signal from the generator after it has been implanted to "tune" the same to the patient. The prosthesis may be designed to be turned on manually when the patient senses the imminence of a convulsion. Alternatively, sensors may be provided for determining changes in the values of state parameters such as electroencephalographic waves which precede a convulsion. The pulse generator can then be turned on automatically in response to the sensors.

17 Claims, 2 Drawing Sheets

NEUROCYBERNETIC PROSTHESIS

CROSS-REFERENCE TO RELATED APPLICATION

This application is a division of application Ser. No. 113,601 filed Oct. 26, 1987, now U.S. Pat. No. 4,867,164, which was a continuation-in-part of prior application Ser. No. 814,846 filed Dec. 30, 1985, now U.S. Pat. No. 4,702,254 which was a continuation-in-part of prior application Ser. No. 531,955 filed Sept. 14, 1983, now abandoned.

BACKGROUND OF THE INVENTION

The present invention is directed toward a medical prosthesis and more particularly toward a medical prosthesis for alleviating or preventing epileptic seizures and other clinical conditions of the nervous system.

Certain diseases or malfunctions of the nervous system are associated with abnormal neural discharge patterns. Some of these are more or less continuous or chronic, such as is the case with Parkinsonism. Others may be discontinuous, characterized by threshold phenomena, such as in epilepsy. The time of onslaught of grand mal or petit mal seizures is often predictable by neural discharge monitoring or other means, even when the exact causal nature of the precipitating dysfunction is not understood.

It is recognized, however, and confirmed by experimentation, that the introduction of certain control signals of the proper configuration, intensity and duration can act as a means for discharging or modifying hyperactivity in the brain. The superposition of such corrective measures, whether by the generation of proper interference patterns overriding control pulses or cancelling signals, acts in a way to inhibit the normal progress of the seizure and may prevent it altogether. It is also possible that control signals of proper magnitudes when applied to associated neural tracts can cause neural activity to return to its normal state.

Corrective signals of this type can be generated by appropriate electrical pulses or waves applied to neurons. Neurons produce electrochemical signals called action potentials which can be triggered by electronic devices.

The primary intent of the present invention is the implantation of a neurocybernetic prosthesis in the human for epileptic control. The operation of the prosthesis is based on the principle of augmenting inhibitory processes in the brain to control states of hypersynchronous neural discharge.

Currently, approximately seventy-five percent of epileptics are responsive in some degree to drugs, although undesirable side effects may force discontinuance. Drug therapy necessitates a continual, general effect on brain cells and other tissues, not infrequently resulting in undesirable side-effects whereas epilepsy constitutes an interrupted condition occurring at an approximate average of two convulsions per week. Unlike drug therapy, a neurocybernetic prosthesis can be made operational just during the period of the convulsion by utilizing sensor feedback or manual control. Also, objective evaluation of drug effectiveness involves determination of chemical levels in the blood which is a very costly procedure. Since hyperactivity of the brain is the basis of many nervous system ailments such as Parkinson's disease, cerebral palsy, spasticity, motor disorders, etc., such a prosthesis would also be useful for these chronic nervous illnesses.

An attempt had been made in the past to provide a neurocybernetic prosthesis for alleviating epilepsy and other disorders. It did not, however, meet with much success for several reasons. This prior attempt included a device which had to be implanted into the brain (cerebellum) thereby requiring expensive and extremely risky brain surgery. Furthermore, the implanted device was found to produce tissue trauma in the cranium. It was found that there was a progressive deterioration of cell bodies in the cerebellar cortex due to the electrical current and excessive regeneration of connective tissue.

SUMMARY OF THE INVENTION

The present invention is designed to obviate the need for brain surgery and the resulting tissue trauma caused thereby and to reduce or eliminate an epileptic's dependence on drugs. The prosthesis of this invention includes a miniature electronic integrated circuit whose output augments appropriate brain neural discharge to control convulsions or seizures. The circuitry and tattery pack are preferably enclosed in an epoxytitanium shell so that the entire device can be totally implanted, preferably in the axilla. Electrode leads pass from the circuit through a subcutaneous tunnel formed toward the neck. The leads terminate in an electrode cuff or patch on the vagus nerve.

The device can be operated either by sensor feedback or manual control and has the capability of regulating aberrant brain signals capable of initiating a convulsive disorder. The principle of design of the neurocybernetic device is based on augmenting central inhibitory processes to regulate the central excitatory state in order to prevent hypersynchronous activity leading to a convulsion. It, therefore, has direct applicability to epilepsy and other nervous system illnesses where convulsions or convulsion-like states obtain.

BRIEF DESCRIPTION OF THE DRAWINGS

For the purpose of illustrating the invention, there are shown in the accompanying drawings forms which are presently preferred; it being understood that the invention is not intended to be limited to the precise arrangements and instrumentalities shown.

Description of the Invention

Figure 1:
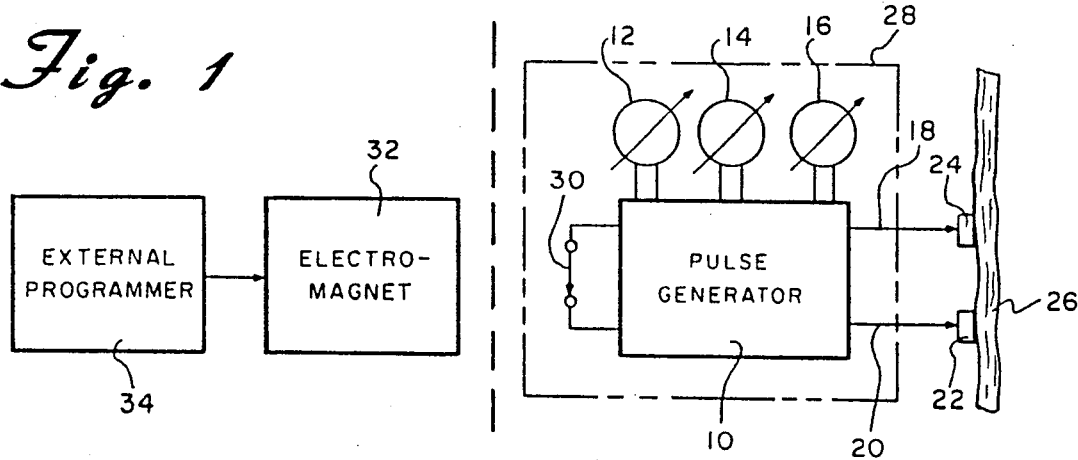
FIG. 1 is a schematic representation of a totally implanted neurocybernetic prosthesis constructed in accordance with the principles of the present invention and showing the manner in which the same is tuned.

The present invention operates utilizing a principle called neurocybernetic spectral discrimination and works in the following way. Since, in general, nerves are of a microscopic diameter and are combined together in a nonhomogeneous mixture of diameters and functional properties, it is not presently possible to adequately control external current to selectively activate a specific group of nerves embedded within a relatively large number of other nerves. Spectral discrimination acts to overcome this fundamental problem by "tuning" the external current (electrical generator) to the electrochemical properties of the selected nerves.

The electrochemical properties utilized in the design of the discriminator are: action potential, conduction velocity, refractory period, threshold, resting membrane potential and synaptic transmission. In addition, there are two general properties of the brain called central excitatory state and hypersynchronicity which can be explained in the following manner.

All nerves can be divided into two functional types: excitatory and inhibitory. The spectral discriminator acts to selectively activate those inhibitory nerves which can prevent or block the epileptic seizure. In other words, these specific inhibitory nerves are embedded in a bundle or cable of nerve fibers of varied functions and properties. A bundle of such nerves may typically consist of 100,000 or more individual fibers and contain mixed excitatory and inhibitory characteristics. The purposeful design of the discriminator is to activate just those relatively few nerves which are inhibitory to the epileptic seizure.

Thus, it must be possible to "discriminate" those desired fibers within a broad spectrum of nerves. One reason that this is important is that if excitatory fibers are simultaneously activated with inhibitory fibers then the desired effect of inhibition on the seizure may be nullified. There is a balance of excitation and inhibition in the brain called the central excitatory state which is affected by specific electrochemical signals. Epilepsy is the increase of the central excitatory state to an abnormal level as based on a hypersynchronous discharge of neurons. A second reason for spectral discrimination is to prevent undesirable side-effects by activating other nerves unnecessarily.

There is a physiological basis for the effectiveness of the selected nerves in blocking or preventing epileptic seizures. The activation of these nerves produces an effect on the reticular system via synaptic transmission. The reticular system has been demonstrated to be important in whatever abnormality leads to epileptic seizures. The reticular system is a relatively large and inhomogeneously constituted structure extending from the hind-brain (medulla) to the mid-brain (thalamus) with neural connections to the cerebral cortex and spinal cord. It is not practical at present to directly electrically activate the reticular system because of its large extent and proximity to vital centers Thus, it was important to discover what nerves might innervate the reticular system sufficiently to produce a significant effect on the reticular system; the net effect being to produce inhibition of epileptic seizures.

For the purpose of interfacing the prosthesis with the critical processes of the brain, inhibition can also be called by its comparable engineering term of negative feedback. Further, it is possible that the seizure originates due to a temporary lack of diminution of negative feedback from the reticular system to seizure sites in the brain. By acting on appropriately selected nerves, the prosthesis results in the replacement of this negative feedback and thus prevents the seizure.

The approach of spectral discrimination is to utilize the basic properties of conduction velocity, diameter, refractory period, threshold, membrane potential, action potential, after potentials, synchronization and synaptic transmission. Based on these properties, the parameters of the pulse generator are chosen in terms of frequency, duration of pulse wave, shape of wave, voltage or current and duration of pulse train. In addition, a time-dependent direct current polarization of the membrane can be utilized to produce a "gate" effect.

The "gate" effect is based upon the polarization characteristics of the neural membrane The membrane potential across the neural membrane can be increased to a point where a block of conduction results. It is a method of separating relatively slower conducting fibers from faster conducting fibers. For example, when the nerve is activated, the action potentials of higher velocity (A) will lead the slower ones (C). A "polarization" block on the nerve membrane will stop A and then the block is removed before C arrives so that the net result is that A, but not C, is prevented from continuing.

The next step is to determine the locus of action of the current generated by the spectral discriminator. This problem relates to the important area of interface between the electronic pulse generator and control signal generated within the brain. In addition, this interface should be of such a nature that the pulse generator is located external to the brain but at the same time the current be set in a compact and identifiable region of nerves so that the site of current is specific and reproducible from patient to patient; no cell bodies are located within the targeted area for current (due to possible production of cell deterioration by the current); and the nerves produce the desired effect on brain operations via sites of synaptic connection.

Analysis by spectral discrimination has demonstrated that the most desirable extra-cranial sites for all these effects are the cranial nerves. Specific cranial nerves have been determined to be optimum for beneficial effects on neurological problems. In particular, the vagus nerve is the optimum site for control of epileptic seizures.

If the total spectrum of the nerve is not known, it is possible to activate all the nerve fibers by the spectral discriminator and record the response on an oscilloscope. From this total fiber spectrum, it is possible to determine the settings of the spectral discriminator to select the activation of the appropriate subset of nerves.

Thus, it is possible to identify by the operation of the spectral discriminator those nerves which can produce the desired corrective signal. Spectral discrimination is not only a therapeutic prosthesis method but it is also the method of analysis to determine nervous system sites for beneficial effects in neurological problems.

In one form of the present invention, the neurocybernetic prosthesis need be turned on only during the duration of a seizure. It can be turned on either manually (by the patient) or automatically by a sensor-feedback system. Many epileptics have sensor signs immediately preceding the convulsion called an aura. At the initiation of the aura, the patient will be able to turn on the device and prevent the seizure. On the other hand, the neurocybernetic prosthesis can include a sensor-feedback system to block the seizure automatically. This feedback system would include sensors specifically designed to determine relatively instantaneous changes in the values of state parameters, which precede eruption of the hypersynchronous activity. Such parameters might include electroencephalographic waves, respiration changes, heart rate changes, various auras or motor effects such as tics or myoclonic jerks. The prosthesis thereby can be activated by sensor feedback producing a signal which precedes convulsive hypersynchronous discharge.

It has also been shown that the neurocybernetic prosthesis can be used prophylactically. That is, the prosthesis can be activated periodically whether or not an aura or other condition is sensed. Preferably, during a treatment period, the prosthesis may be activated once every hour or so for a minute or more with the frequency and duration gradually reduced to nothing at the end of the period which may be several hours or a week or more. Such treatment can eliminate seizures or at least reduce their frequency and intensity. This continuous cycling on and off is also most useful for treating continuous or chronic tremors such as Parkinsonism.

One example of an electrical circuit for practicing the present invention is shown schematically in FIG. 1. The circuit is comprised essentially of a pulse generator 10 which is capable of generating electrical pulses having a frequency of between 30 and 300 cycles per second, a pulse duration of between 0.3 and 1 millisecond and a constant current of between approximately 1 and 20 milliamperes. The frequency, pulse width and the voltage or current level of the output signal from the pulse generator can be varied by controls 12, 14 and 16. Although the pulse width and current or voltage are set by the controls 14 and 16, it is preferred that the generator 10 be of the type which is capable of ramping up to the set pulse width and/or current or voltage whenever the generator is activated. This technique helps to eliminate involuntary twitching when the prosthesis is activated and is particularly useful when continuous types of tremors are being controlled or suppressed by the prosthesis. Electrode leads 18 and 20 are connected to electrodes 22 and 24 which are applied to the vagus nerve 26 in a manner to be more fully described hereinafter.

In the preferred embodiment of the invention, the pulse generator 10 with its battery pack and other associated circuits are preferably intended to be fully implanted. For this reason, the generator is enclosed in an epoxy-titanium shell 28 (or similar bio-compatible material). As described above, the present invention operates utilizing the principle of neurocybernetic spectral discrimination. The prosthesis must, therefore, combine the desired current parameters to correspond to the specific properties (linear and non-linear) of the selected nerves. Thus, the command signal of the device is a function of the following specific nerve properties: refractory periods, conduction velocity, synchronization or de-synchronization, threshold and brain inhibitory state. In a sense, the current parameters must be "tuned" to the specified nerve properties.

It is for the foregoing reason that the pulse generator 10 is provided with the means 12, 14 and 16 for varying the various current parameters of the pulse signal. The desired parameters are chosen by applying the electrodes 22 and 24 to the vagus nerve and varying the current parameters until the desired clinical effect is produced.

Since this "tuning" may have to be performed after the pulse generator is implanted, the present invention provides a means for varying the current parameters percutaneously. This is accomplished by a reed switch 30 associated with the implanted pulse generator 10 which is remotely controlled by electromagnet 32 and external programmer 34. The precise manner in which this is accomplished and the circuitry associated therewith is well known to those skilled in the art as the same technique has been widely used in connection with the "tuning" of cardiac pacemakers.

Even though a particular frequency or narrow band of frequencies is required for the desired purpose, it is believed that results may also be obtained by a variable frequency signal. If the frequency is varied by sweeping up and down by a random signal circuit or some other algorithm, there would be assurance that the proper frequency signal would be applied at least some of the time.

Figure 2:
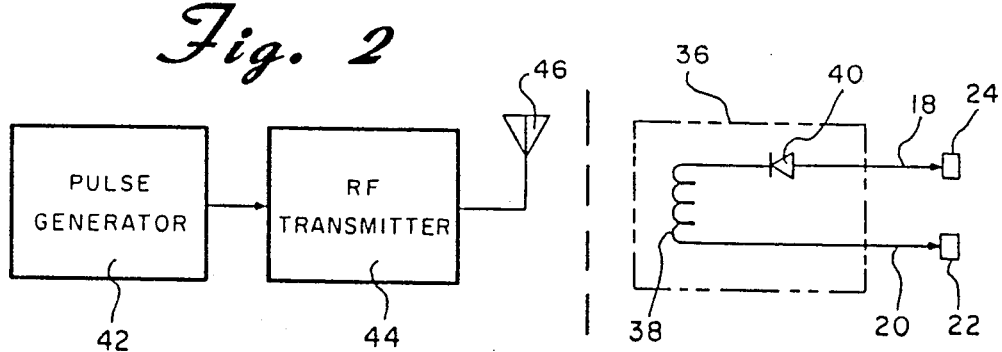
FIG. 2 is a schematic representation of a partially implanted neurocybernetic prosthesis.

The device shown in FIG. 1 is intended for full implantation. It is also possible to practice the present invention with partial implantation. This is accomplished as shown in FIG. 2 by the use of a receiver 36 including a coil 38 and diode 40. The receiver is enclosed in an epoxytitanium shell so that it can be implanted and is connected to the electrodes 22 and 24 on the vagus nerve through leads 18 and 20.

Located percutaneously is a pulse generator 42 which modulates the radio frequency transmitter 44 and delivers the radio frequency signal to antenna 46 which transmits the same to the receiver 36 when desired. It should be readily apparent that pulse generator 42 is also capable of being tuned so that the desired current parameters can be obtained. The pulse generator 42, transmitter 44 and antenna 46 could either be permanently worn on a person's body in the vicinity of the receiver 36 so that it need only be turned on when necessary or it may be separately carried in a person's pocket or the like and used whenever needed.

When the neurocybernetic prosthesis of the present invention is utilized for preventing epileptic seizures, it can be utilized as described above wherein the current generator is turned on only immediately preceding a convulsion. Many epileptics have sensory signs immediately preceding the convulsion called an aura. At the initiation of the aura, the patient will be able to turn on the device to prevent the seizure through the use of a manually operated switch. Even with a fully implanted prosthesis, a momentary contact switch, magnetically operated reed switch or a number of other devices could be provided which could be activated from outside of the body.

Figure 3:
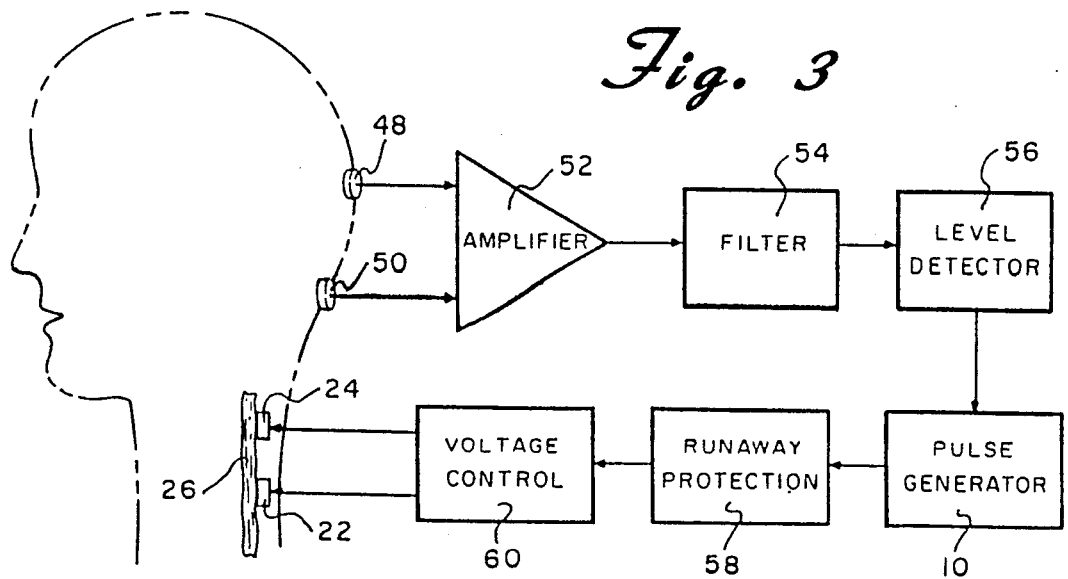
FIG. 3 is a schematic representation of a sensor-feedback system for automatically initiating the neurocybernetic prosthesis.

It is also possible to provide the prosthesis with a sensor-feedback system to block the seizure automatically. An example of such a system is shown in FIG. 3 and includes additional scalp electrodes 48 and 50 for measuring electroencephalographic waves. The output of the electrodes 48 and 50 is amplified by amplifier 52 and is then passed through filter 54 to level detector 56. When level detector 56 senses a significant and predetermined change in the electroencephalographic wave signal, it will automatically initiate the pulse generator 10 which will apply the required pulses to the electrodes 22 and 24 through runaway protection circuit 58 and voltage control circuit 60.

Although the sensing of electroencephalographic waves has been used above as an example for automatically turning on the neurocybernetic prosthesis, it should be apparent that other state parameters can be measured to provide a sensor-feedback system. Such other parameters might include respiration changes, heart rate changes, various auras or motor effects such as tics or myoclonic jerks. As a result, the prosthesis can be activated by sensor feedback producing a signal which precedes convulsive hypersynchronous discharge.

Figure 4:
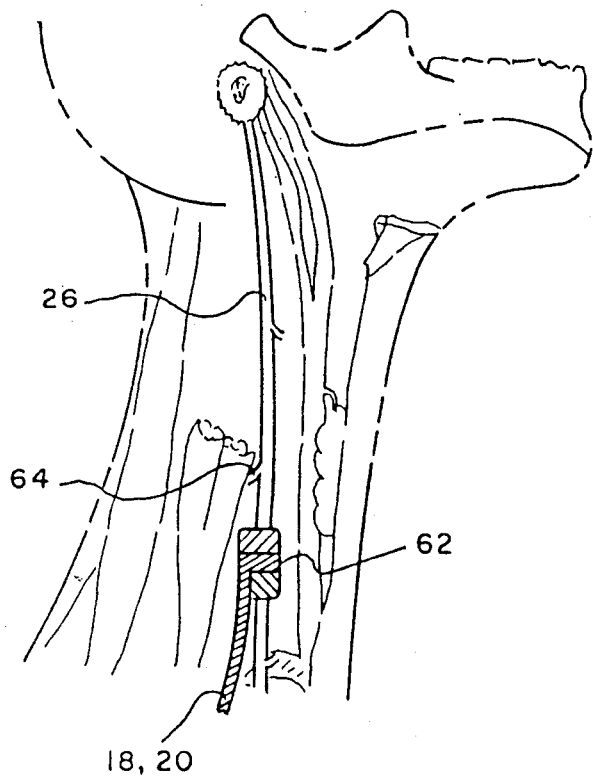
FIG. 4 schematically illustrates the placement of an electrode patch on the vagus nerve and the relationship of the vagus nerve with adjacent structures, and FIG. 5 schematically represents the preferred placement of the pulse generator and electrode patch of the present invention in the human body.

FIG. 4 illustrates the placement of the electrodes on the vagus nerve and shows the relationship of the vagus with adjacent structures. The electrodes are shown as a single electrode patch 62 which is known per se. Electrode patch 62 includes both the positive and negative electrodes.

Although it is theoretically possible to place the electrode patch 62 or separate electrodes substantially anywhere along the length of the vagus nerve 26, minimal slowing of the heart rate is achieved by placing the same below the inferior cardiac nerve 64. The electrodes may be placed on or adjacent to the vagus. It is preferred, however, that the negative electrode be proximal to the brain and the positive electrode be distal thereto. In certain instances, the positive electrode may be used as an indifferent electrode and be placed in a different part of the body. For example, the case 26 of the implanted pulse generator 10 could, in some instances, be utilized as the positive electrode. It should be readily apparent to those skilled in the art that the terms "positive electrode" and "negative electrode" are merely relative; a positive electrode being one which is more positive than a negative electrode. Similarly, a negative electrode is one which is more negative than a positive electrode.

An electrode patch or cuff electrode such as that shown in FIG. 4 is the preferred embodiment. However, it should be readily apparent to those skilled in the art that various known electrodes such as a tripolar cuff electrode could be utilized. The electrodes may be placed either in direct contact with the nerve or in indirect contact with the neural tissue. There is no indication that placement of state of the art electrodes on the nerve itself would have a deleterious effect unless silver electrodes are utilized.

Figure 5:
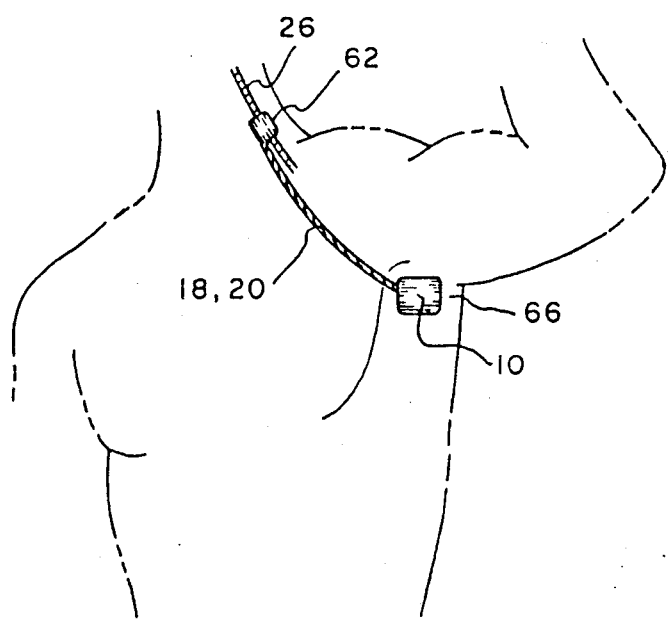

As shown in FIG. 5, the axilla or armpit 66 is the preferred location for placement of the pulse generator 10. The axilla provides protection for the pulse generator while allowing freedom of movement and is in proximity to the electrode patch 62. A subcutaneous tunnel between the incision made to implant the electrode patch and the incision made for implanting the pulse generator can be made with a metal rod. A plastic tube can then be inserted in the tunnel through which the electrode leads 18 and 20 can pass without excessive traction.

The present invention may be embodied in other specific forms without departing from the spirit or essential attributes thereof and accordingly, reference should be made to the appended claims rather than to the foregoing specification as indicating the scope of the invention.

I claim:

1. A method of controlling or preventing epileptic seizures comprising applying a pulsed electrical signal to the vagus nerve in such a way as to avoid any substantial slowing of the heart rate, said signal being applied repeatedly over a period of time to thereby prevent or control such seizures.

2. The method of claim 1 wherein the electrical signal has a pulse frequency of approximately between 30 and 300 cycles per second and wherein each pulse has a duration of between 0.3 and 1 millisecond and substantially constant current of between approximately 1 and 20 milliamperes.

3. The method of claim 1 wherein the signal is applied utilizing a plurality of electrodes.

4. The method of claim 3 wherein there is a negative electrode and a positive electrode and wherein the negative electrode is applied proximal to the brain and the positive electrode is applied distal thereto.

5. The method of claim 3 wherein there is a negative electrode and a positive electrode and wherein the negative electrode is placed in the vicinity of the vagus nerve and the positive electrode is applied to a remote part of the body.

6. The method of claim 1 further including the step of first determining that an epileptic seizure is going to occur and thereafter applying said signal.

7. A method of controlling or preventing epileptic seizures comprising applying a pulsed electrical signal to the vagus nerve at a point below the inferior cardiac nerve, said signal being applied repeatedly over a period of time to thereby prevent or control such seizures.

8. The method of claim 7 wherein the electrical signal has a pulse frequency of approximately between 30 and 300 cycles per second and wherein each pulse has a duration of between 0.3 and 1 millisecond and substantially constant current of between approximately 1 and 20 milliamperes.

9. The method of claim 7 wherein the signal is applied utilizing a plurality of electrodes.

10. The method of claim 9 wherein there is a negative electrode and a positive electrode and wherein the negative electrode is applied proximal to the brain and the positive electrode is applied distal thereto.

11. The method of claim 9 wherein there is a negative electrode and a positive electrode and wherein the negative electrode is placed in the vicinity of the vagus nerve and the positive electrode is applied to a remote part of the body.

12. The method of claim 7 further including the step of first determining that an epileptic seizure is going to occur and thereafter applying said signal.

13. A method of controlling or preventing epileptic seizures comprising determining that a seizure is going to occur and thereafter applying a pulsed electrical signal to the vagus nerve to thereby prevent or control such seizure.

14. The method of claim 13 wherein the electrical signal has a pulse frequency of approximately between 30 and 300 cycles per second and wherein each pulse has a duration of between 0.3 and 1 millisecond and substantially constant current of between approximately 1 and 20 milliamperes.

15. The method of claim 13 wherein the signal is applied utilizing a plurality of electrodes.

16. The method of claim 15 wherein there is a negative electrode and a positive electrode and wherein the negative electrode is applied proximal to the brain and the positive electrode is applied distal thereto.

17. The method of claim 15 wherein there is a negative electrode and a positive electrode and wherein the negative electrode is placed in the vicinity of the vagus nerve and the positive electrode is applied to a remote part of the body.

* * * * *